United States Patent [19]
Mason et al.

[11] 4,289,122
[45] Sep. 15, 1981

[54] ANKLE-FOOT ORTHOSIS

[76] Inventors: Randy D. F. Mason, 3825 Sierra Morena, Carlsbad, Calif. 92008; William Vuletich, 1210 Caminito Septimo, Cardiff, Calif. 92007

[21] Appl. No.: 32,568

[22] Filed: Apr. 23, 1979

[51] Int. Cl.³ .......................... A61F 3/00; A61F 5/04
[52] U.S. Cl. ................................ 128/80 E; 128/80 H; 128/89 R
[58] Field of Search ................ 128/80 E, 80 H, 87 R, 128/88, 89 R, DIG. 15, 90

[56] References Cited
U.S. PATENT DOCUMENTS

| | | | |
|---|---|---|---|
| 1,232,899 | 3/1917 | De Puy | 128/89 R |
| 1,708,757 | 6/1929 | Freileweh | 128/80 H |
| 3,528,412 | 9/1970 | McDavid | 128/89 R |
| 3,618,946 | 11/1971 | Lee | 128/80 R |
| 3,680,549 | 8/1972 | Lehneis et al. | 128/89 R |
| 3,750,660 | 8/1973 | Muller | 128/89 R |
| 4,166,460 | 9/1979 | Applegate | 128/80 H |

OTHER PUBLICATIONS

"Atlas of Orthotics of the American Academy of Orthopaedic Surgeons", Pub. by Mosby Co., 1975, pp. 206, 208, 213.
"Orthotics Etcetra", by S. Licht & H. L. Kamenetz, Waverly Press, Inc., Baltimore, Md. 1966, pp. 251, 257.

Primary Examiner—Robert W. Michell
Assistant Examiner—C. W. Shedd
Attorney, Agent, or Firm—Henri J. A. Charmasson

[57] ABSTRACT

An ankle-foot orthosis made of thin-sheeted polypropylene material which comprises a foot section and a leg section articulately attached to one another on each side of the ankle in order to facilitate dorsi-flexion. The leg section has a flanged lower lip overlapping the upper edge of the foot section. The overlap provides a stop for the backward movement of the leg section around the articulation point, thus limiting plantar flecion and foot drop.

4 Claims, 12 Drawing Figures

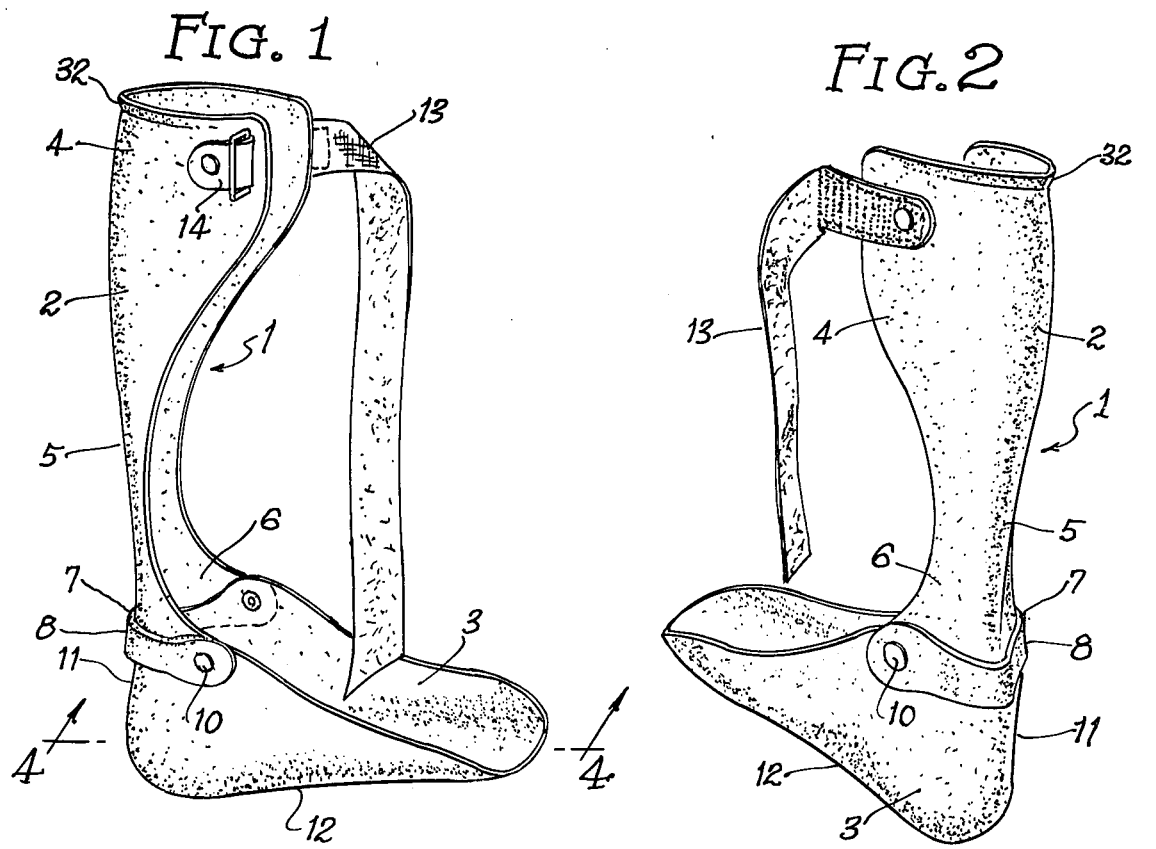
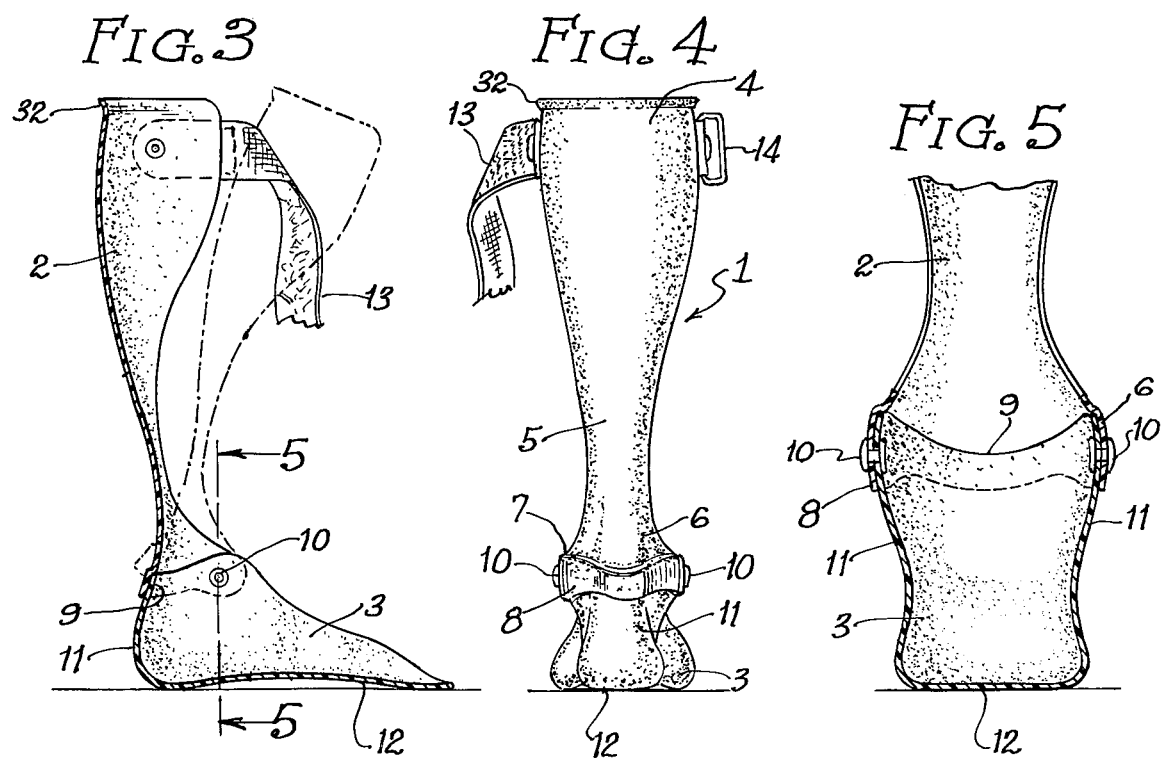

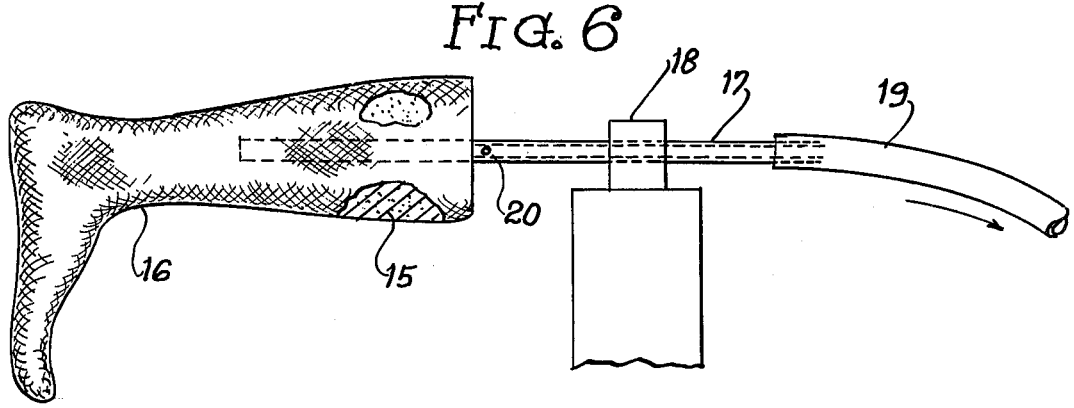
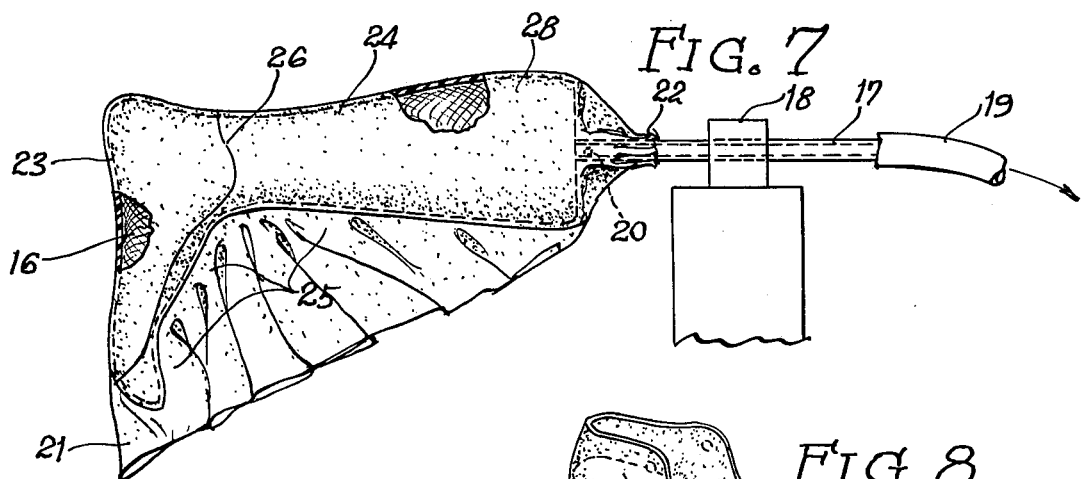
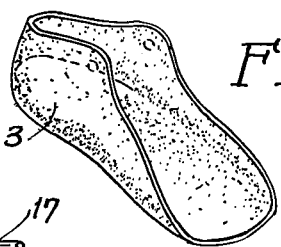
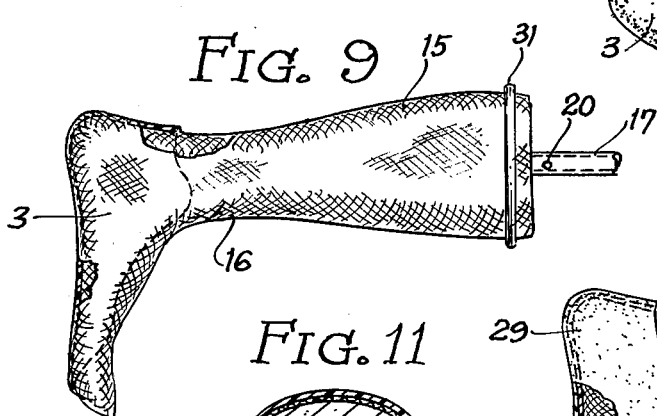
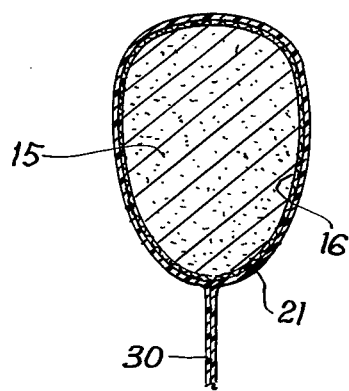
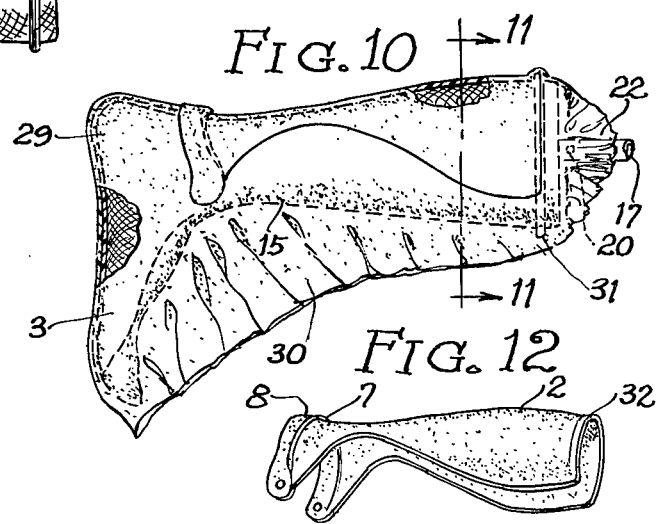

ANKLE-FOOT ORTHOSIS

BACKGROUND OF THE INVENTION

The invention relates to orthopedic braces and more particularly to pivotable leg and foot braces designed to facilitate dorsi-flexion while providing metatarsal support and correcting foot drop. In the past such biomechanical purposes have been achieved by devices comprising a pair of metal uprights attached to the patient's calf and extending down along each side of the leg to the level of the ankle. A stirrup-type shoe attachment with upward projections pivotally attached to the uprights completed the brace. The ankle joints were engineered to provide a stop limiting the backward movement of the leg. Springs were sometimes added to the joint to provide dorsi-flexion assistance during swing phase of a step. This type of brace was rather cumbersome, unsightly, and costly due to the multiplicity of components used in this fabrication. More recently foot support made of plastic laminate molded around the plantar and heel section of the foot have been combined with metal uprights to provide a brace which can be inserted into a regular shoe. However, the metallic joints offer many pinching and shearing areas in which materials from the stockings, shoes or trousers tend to be caught. There is, thus, need for an ankle-foot orthosis made of thin-sheeted material which could be installed in intimate contact with the patient's foot and leg and yet provide an articulation about the ankle area free from any pinching surfaces, so that it could be worn inside a shoe or even under a stocking.

SUMMARY OF THE INVENTION

It is the principal object of this invention to provide a lightweight ankle-foot orthosis with an articulation about the ankle area.

A further object of the invention is to provide an articulated ankle-foot orthosis which limits the plantar flexion.

Another object of the invention is to provide such an orthosis which may be inserted in a regular shoe or worn under a stocking.

An additional object of this invention is to provide an ankle-articulated orthosis devoid of any pinching surfaces.

It is also the object of this invention to provide a convenient method for the fabrication of such orthosis.

These and other objects of the invention are achieved by an ankle-foot orthosis made of thin-sheeted polypropylene material which comprises a foot section and a leg section contoured to intimately support the patient's limb with a pivotal articulation on each side of the ankle. The leg section has a flanged lower lip overlapping the upper edge of the foot section which provides a stop for the backward movement of the leg section while shielding the pinching surfaces from the stockings or shoe material. Proper fitting of the overlapping areas of the orthosis is obtained by way of a two-step molding process.

BRIEF DESCRIPTION OF THE DRAWING

FIG. 1 is a frontal perspective view of the ankle-foot orthosis;

FIG. 2 is a back perspective view thereof;

FIG. 3 is a cross sectional view taken along line 4—4 of FIG. 3;

FIG. 4 is a back elevational view of the orthosis;

FIG. 5 is an enlarged, partial, cross sectional view taken along lines 5—5 of FIG. 3;

FIG. 6 is a front elevational view of the apparatus used in fabricating the ankle-foot orthosis;

FIG. 7 illustrates the first step in the manufacture of the ankle-foot orthosis;

FIG. 8 is a perspective view of the plantar section obtained through the first manufacturing step;

FIG. 9 is a frontal view of the mold dressed in preparation of the second manufacturing step;

FIG. 10 illustrates the second step in the manufacturing of the ankle-foot orthosis;

FIG. 11 is a cross sectional view taken along line 11—11 of FIG. 10; and

FIG. 12 is a perspective view of the leg section made in accordance with the second manufacturing step.

DESCRIPTION OF THE PREFERRED EMBODIMENT OF THE INVENTION

Referring now to FIGS. 1 through 5 of the drawing, and in accordance with the invention, there is illustrated an ankle-foot orthosis 1. The orthosis 1 comprises two sections: a greave 2 or leg section, and a plantar section 12. The two sections 2 and 3 are articulately joined on each side of the ankle by two rivets 10. The greave 2 comprises an upper portion for wrapping around the patient's calf which can be secured to the calf by a Velcro ® type strap 13. The strap 13 is attached to one side of the greave, its free end being designed to loop around a ring 14 attached to the other side of the greave. The greave 2 extends downward from the calf area to form a narrow shank 5. Below the shank 5 the greave broadens into a lower portion which wraps around the ankle area. The plantar section 3 has a rigid sole 12 and an upward projection 11 which intimately wraps around the heel and ankle areas of the patient. The lower broadening portion 6 of the greave 2 overlaps the upper edge of the upward projection 11 of the plantar section 3 when the patient's foot is roughly perpendicular to the leg. The lower portion 8 of the greave 2 which overlaps the upper edge of the plantar section 3 projects outward above the outside surface of the greave 2, forming a small shoulder 7 which matches the outline of the upper edge of the plantar section. The rivets 10 are mounted loosely so that the plantar section 3 can rotate upward around the axis delineated by the two rivets 10. This movement of the plantar section 3 provides for dorsi-flexion of the foot during the swing phase of a step. The downward movement of the plantar section 3 is stopped when the upper edge of the projection 11 comes into contact with the ledge on the inside of the greave 2 opposite the shoulder 7, thus preventing patient's foot drop. The two sections 2 and 3 of the orthosis are made from thin-sheeted polypropylene material and are contoured to intimately follow the patient's leg and foot outline. The orthosis can thus be worn above or under a stocking; and with normal footwear. The overlapping portion 8 of the greave 1 will keep the stocking or shoe material from being pinched between the lower edge of the greave 2 and the upper edge of the plantar section 3 when the patient is walking.

The shank area 5 of the greave 2 may be trimmed down to provide a certain amount of backward resilient flexibility for the maximum comfort of the patient.

Preferably, the orthosis is cast from a exact plaster replica of the patient's foot and leg as further described below.

Referring now to FIGS. 6 through 12, there is illustrated the manufacturing process followed in the fabrication of the ankle-foot orthosis 1. Firstly, a plaster model 15 of the patient's foot and leg is made. This may be done by first making a plaster cast around the leg and foot of the patient. The cast is then cut open and removed from the leg. The empty cast is then reassembled and plaster is poured into it to create a positive mold of the patient's limb. Before the plaster solidifies the end of a tube 17 is implanted in the middle of the leg. The tube has a small hole 20 drilled just above the surface of the plaster mold. The mold and tube are held horizontally with toes pointing downward by a vice 18. The open end of the tube 17 is connected to a vacuum pump by means of a hose 19. The mold 15 is then covered with a nylon stocking 16. A sheet 21 of polypropylene material is preheated to a near molten state, then wrapped around the mold 15 and part of the tube 17. The sheet 21 is pulled tight over the calf, ankle and heel of the mold 15. The envelope-forming sheet 21 is then pressure-sealed around the tube 17 at 22 and along a line 25 running down the chin all the way to the toes. Air is drawn through hole 20 by the vacuum pump, causing the polypropylene sheet 21 to adhere tightly to the surface of the mold 15. The polypropylene sheet 21 is cooled down to a solid state. The part enveloping the foot is cut along line 26 of FIG. 7 to obtain the foot section 3 of the orthosis shown in FIG. 8. The remainder 28 of the polypropylene sheet 21 is discarded. The foot section 3 is now mounted back upon the mold 15 under the stocking 16. A second sheet 30 of preheated polypropylene is wrapped around the mold and sealed as previously explained around tube 17 and the mold 15. The vacuum process is repeated and after a cooling period the greave or leg part of the orthosis is cut out along line 27 of FIG. 10. In the latter process, care is taken to include as part of the lower part of the greave 2 a narrow band 8 overlapping the upper edge of the foot section 3. The flanged upper edge 32 of the greave 2 is obtained by placing a rubber ring 31 around the upper end of the mold 15 before applying the polypropylene sheet 30.

The two-step process that we have just described guarantees that the inside surface of the orthosis will intimately match the outline of the patient's foot and leg. It also provides for a perfect fit between the foot and leg section at the overlapping area 8 and around the pivotal connections on each side of the patient's ankle. It should be clear that the greave 2 could be extended above the knee to form a long-leg orthosis. The process just described could be used to form other types of articulated orthosis designed for intimate body contact.

While we have described the preferred embodiment of our invention, and suggested modifications thereto, other changes could be made and other embodiments could be implemented without departing from the spirit of the invention and from the scope of the appended claims.

The invention claimed is:

1. An ankle-foot brace securable to a patient's leg for controlling the ankle movement which comprises:
   a unitary plantar element made of hard, thin-sheeted material having an upward projection shaped and dimensioned to wrap intimately around the heel and ankle area;
   a unitary leg element made of hard thin-sheeted material having an upper portion shaped and dimensioned to wrap intimately around the calf, a shank extending downward from said upper portion along the back of the lower leg, a broadening lower portion at the lower end of said shank partially extending over said projection and over both sides of said ankle area, and means for securing said upper portion to the leg;
   means for pivotally attaching the upward projection of the plantar element to the broadening lower portion of the leg element at ankle level about the normal flexure axis of the ankle; and
   means integral with said plantar element and said leg element for limiting the backward movement of the leg element in relation to the plantar element.

2. The orthosis claimed in claim 1 wherein said means for limiting comprise:
   at the lower edge of said lower portion an outward projecting rim shaped and dimensioned to cap the upper edge of said upward projection when the leg element is at its maximum backward position in relation to the plantar element.

3. The orthosis claimed in claim 1 or claim 2 wherein said means for attaching comprise a pair of rivets mounted on a common transversal axis on opposite sides of the ankle pivotally and loosely fastening said broadening lower portion to said upward projection.

4. The orthosis claimed in claim 2 wherein said shank comprises a generally narrow, elongated section made of flexible material.

* * * * *